(12) United States Patent
Knepper et al.

(10) Patent No.: US 11,116,931 B2
(45) Date of Patent: Sep. 14, 2021

(54) SYSTEM AND METHOD FOR CONTROLLING CONDUIT HEATING

(71) Applicant: KONINKLIJKE PHILIPS N.V., Eindhoven (NL)

(72) Inventors: Michael B. Knepper, Friedens, PA (US); Steven Adam Kimmel, Delmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 320 days.

(21) Appl. No.: 16/220,018

(22) Filed: Dec. 14, 2018

(65) Prior Publication Data

US 2019/0184129 A1    Jun. 20, 2019

Related U.S. Application Data

(60) Provisional application No. 62/599,867, filed on Dec. 18, 2017.

(51) Int. Cl.
*A61M 16/16*    (2006.01)
*A61M 16/00*    (2006.01)
(Continued)

(52) U.S. Cl.
CPC ...... *A61M 16/161* (2014.02); *A61M 16/0003* (2014.02); *A61M 16/0066* (2013.01); *A61M 16/0069* (2014.02); *A61M 16/024* (2017.08); *A61M 16/1075* (2013.01); *A61M 16/1095* (2014.02); *A61M 16/16* (2013.01); *H02J 1/00* (2013.01); *H05B 1/00* (2013.01); *H05B 3/00* (2013.01); *A61M 16/06* (2013.01); *A61M 16/0633* (2014.02); *A61M 16/0683* (2013.01); *A61M 16/0816* (2013.01); *A61M 16/202* (2014.02); *A61M 2016/0021* (2013.01);
(Continued)

(58) Field of Classification Search
CPC .......... A61M 16/0003; A61M 16/1095; A61M 2016/0021; A61M 2205/3368; H05B 1/00; H05B 3/0014; H05B 3/0019; H05B 3/0085
See application file for complete search history.

(56) References Cited

U.S. PATENT DOCUMENTS 4,574,188 A * 3/1986 Midgley ................ H05B 3/146
  219/505
5,148,802 A    9/1992 Sanders
(Continued)

FOREIGN PATENT DOCUMENTS

WO    WO-2017043981 A1 *  3/2017 ........ A61M 16/0891

*Primary Examiner* — Kathryn E Ditmer
(74) *Attorney, Agent, or Firm* — Michael W. Haas

(57) ABSTRACT

A pressure support system for delivering a flow of breathing gas to an airway of a patient includes a base unit structured to generate the flow of breathing gas and including a heating control unit, a conduit coupled to the base unit and structured to carry the flow of breathing gas, a thermistor disposed in the conduit, and first and second resistive wires extending along the conduit from the base unit to the thermistor. The heating control unit is structured to selectively operate in a first mode to heat the conduit using the first and second resistive wires and a second mode to sense a temperature of airflow in the conduit with the thermistor via the first and second resistive wires.

14 Claims, 7 Drawing Sheets

(51) Int. Cl.
   *A61M 16/10* (2006.01)
   *H02J 1/00* (2006.01)
   *H05B 3/00* (2006.01)
   *H05B 1/00* (2006.01)
   *A61M 16/08* (2006.01)
   A61M 16/06 (2006.01)
   A61M 16/20 (2006.01)

(52) U.S. Cl.
   CPC .............. *A61M 2016/0039* (2013.01); *A61M 2202/0225* (2013.01); *A61M 2205/3368* (2013.01); *A61M 2205/502* (2013.01)

(56) References Cited

U.S. PATENT DOCUMENTS

| | | | |
|---|---|---|---|
| 5,313,937 | A | 5/1994 | Zdrojkowski |
| 5,392,770 | A * | 2/1995 | Clawson ........... A61M 16/1075 128/203.27 |
| 5,433,193 | A | 7/1995 | Sanders |
| 5,632,269 | A | 5/1997 | Zdrojkowski |
| 5,803,065 | A | 9/1998 | Zdrojkowski |
| 6,029,664 | A | 2/2000 | Zdrojkowski |
| 6,539,940 | B2 | 4/2003 | Zdrojkowski |
| 6,626,175 | B2 | 9/2003 | Jafari |
| 7,011,091 | B2 | 3/2006 | Hill |
| 2003/0236015 | A1 * | 12/2003 | Edirisuriya ......... F16L 25/0036 439/191 |
| 2006/0289463 | A1 * | 12/2006 | Kil ........................ G05D 23/24 219/505 |
| 2008/0028850 | A1 * | 2/2008 | Payton .............. A61M 16/1005 73/204.19 |

* cited by examiner

SYSTEM AND METHOD FOR CONTROLLING CONDUIT HEATING

CROSS-REFERENCE TO RELATED APPLICATIONS

This patent application claims the priority benefit under 35 U.S.C. § 119(e) of U.S. Provisional Application No. 62/599,867, filed on Dec. 18, 2017, the contents of which are herein incorporated by reference.

BACKGROUND OF THE INVENTION

1. Field of the Invention

The present invention pertains to airway pressure support devices, and, in particular, to a system and method for controlling conduit heating in a pressure support system.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

"Rainout" is a condition that occurs when the humidity of the air within the air flow path of a pressure support system (e.g. the CPAP unit, hose, and mask) condenses on the inside surfaces of the components of the air flow path, resulting in pooling of water within the airflow path over time (which is a nuisance to the patient receiving therapy). When rainout occurs, it often disturbs the patient, which in turn may cause the patient to discontinue therapy for the remainder of the night. Rainout occurs because the air within the airflow path is heated and humidified by the pressure support device (or the patient's own body in the case of exhaled air), but the temperatures of the walls of the airflow circuit (e.g. a hose or mask) are equilibrated with the ambient environment which may be significantly cooler than the air in the airflow circuit. The temperature of the air within the airflow circuit decreases when it makes contact with the walls of the circuit, resulting in condensation (i.e. "rainout").

Some pressure support systems attempt to reduce rainout by adding heating elements to the walls of the airflow circuit (e.g. a heated conduit). FIG. 1 shows an example of a pressure support system 100 with heating in its conduit 120. Pressure support system 100 includes a base unit 110 including a pressure generating device that generates airflow 125 that is provided to a patient interface device 130 (e.g., without limitation, a mask) via conduit 120.

Base unit 100 includes a heating control unit 111. First, second, and third resistive wires 121,122,123 extend along conduit 120. A thermistor 124 is disposed in conduit 120 to sense the temperature of airflow 125 through conduit 120. Heating control unit 111 includes a first voltage source 113, a second voltage source 114, a first switch 115, and a second switch 116. First voltage source 113 has a higher voltage than second voltage source 114. Voltage from first voltage source 113 is used to provide heating for conduit 120 via second and third resistive wires 122,123. Second voltage source 114 is used to provide a voltage across thermistor 124 to sense the temperature of airflow 125. A neutral reference point 118 (e.g., without limitation, a ground) is also provided in heating control unit 111.

First voltage source 113, first switch 115, second resistive wire 122, third resistive wire 123, and neutral reference point 118 are arranged in series. To provide heating of airflow 125, first switch 115 is closed by a processor 112 in heating control unit 111 which allows current to flow from first voltage source 113 to neutral reference point 118 via second and third resistive wires 122,123. The current heats second and third resistive wires 122,123 which heats airflow 125.

Second voltage source 114, second switch 116, a pull-up resistor 117, first resistive wire 121, thermistor 124, third resistive wire 123, and neutral reference point 118 are arranged in series. To sense temperature of airflow 125 via thermistor 124, second switch 116 is closed by processor 112 which allows current to flow through thermistor 124. Processor 112 is electrically connected to first resistive wire 121 to measure the output of thermistor 124 to determine the temperature of airflow 125.

The pressure support system 100 uses three resistive wires 121,122,123 that extend along conduit 120 to heat and measure a temperature of airflow 125. Each resistive wire adds to the cost of pressure support system 100.

SUMMARY OF THE INVENTION

Accordingly, it is an object of the present invention to provide a pressure support device that overcomes the shortcomings of conventional pressure support devices. This object is achieved according to one embodiment of the present invention by providing a pressure support system for delivering a flow of breathing gas to an airway of a patient that includes a base unit structured to generate the flow of breathing gas and including a heating control unit, a conduit coupled to the base unit and structured to carry the flow of breathing gas, a thermistor disposed in the conduit, and first and second resistive wires extending along the conduit from the base unit to the thermistor. The heating control unit is structured to selectively operate in a first mode to heat the conduit using the first and second resistive wires and a second mode to sense a temperature of airflow in the conduit with the thermistor via the first and second resistive wires.

It is yet another object of the present invention to provide a method of heating airflow in a conduit of a pressure support system. The method includes providing a base unit structured to generate the flow of breathing gas and including a heating control unit, the conduit coupled to the base unit and structured to carry the flow of breathing gas, a thermistor disposed in the conduit, and first and second resistive wires extending along the conduit from the base unit to the thermistor. The method also includes operating the heating control unit in a first mode to heat the conduit using the first and second resistive wires and operating the heating control unit in a second mode to sense a temperature of airflow in the conduit with the thermistor via the first and second resistive wires.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
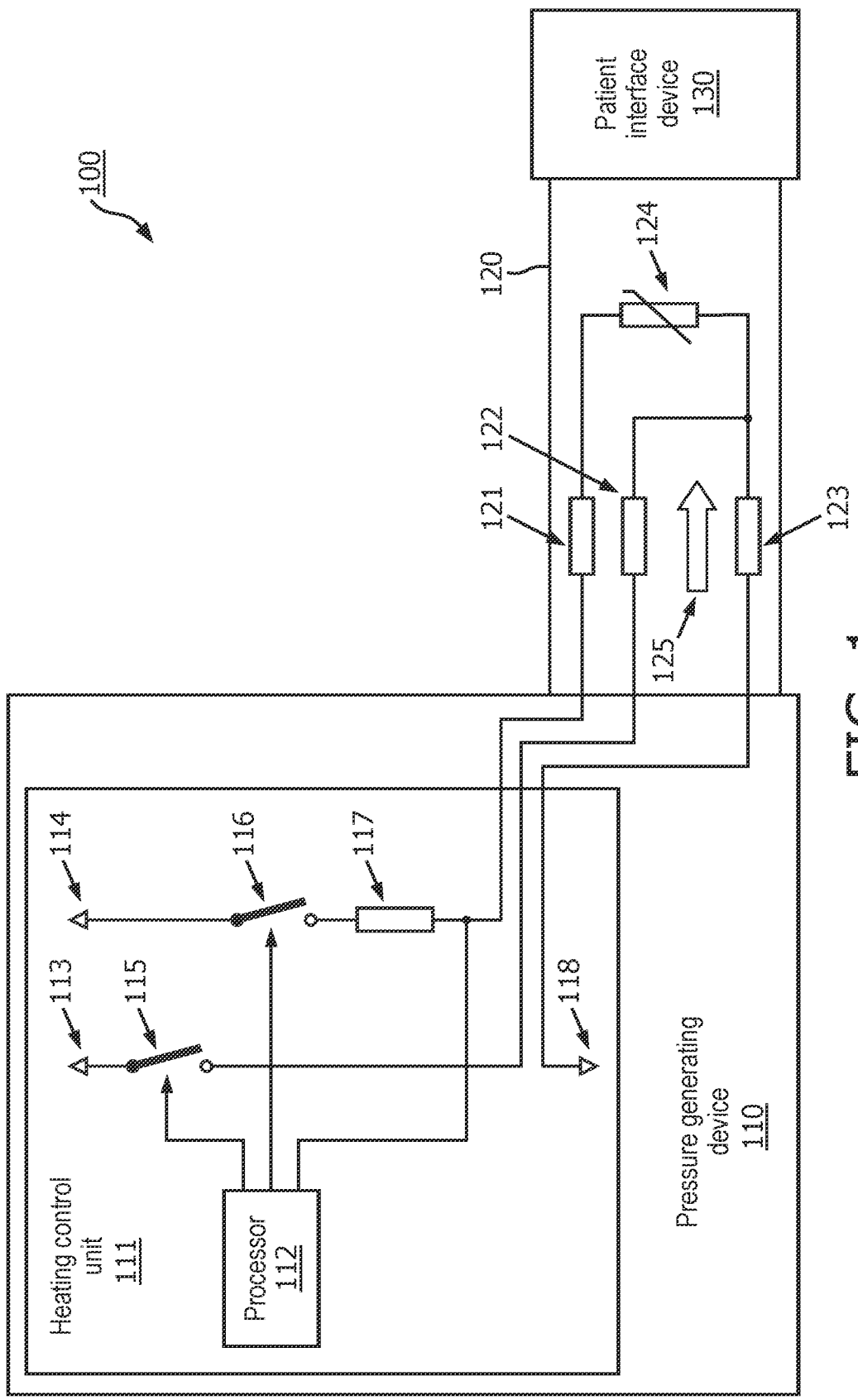
FIG. 1 is a schematic diagram showing an airway pressure support system with a heated conduit.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
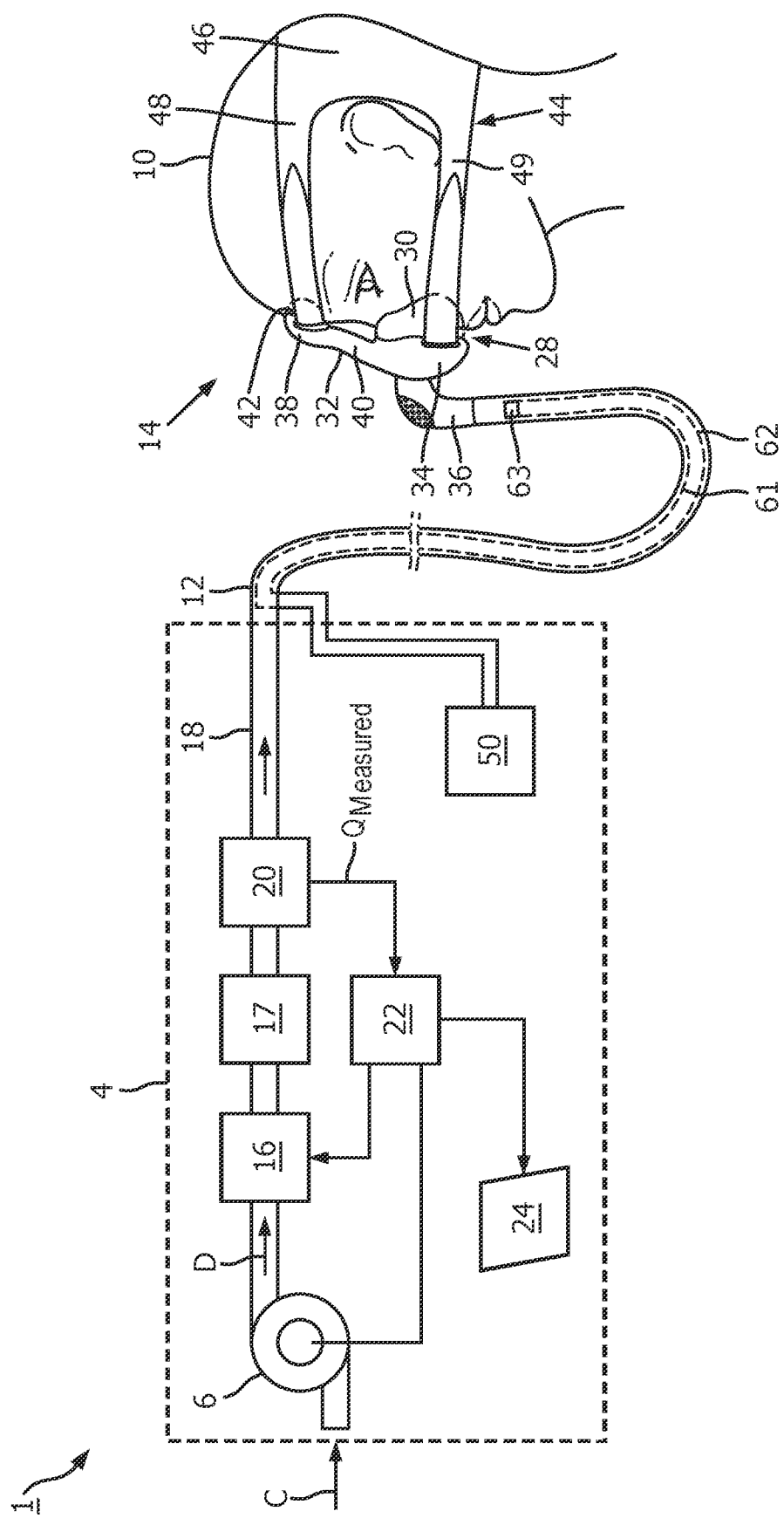
FIG. 2 is a schematic diagram of an airway pressure support system according to an exemplary embodiment.

FIG. 2 is a schematic diagram showing an airway pressure support system 2 according to one particular, non-limiting exemplary embodiment. Airway pressure support system 1 includes a pressure generating device base unit 4 which houses a gas flow generator 6, such as a blower used in a conventional CPAP or bi-level pressure support device. Gas flow generator 6 receives breathing gas, generally indicated by arrow C, from the ambient atmosphere and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cmH2O. The pressurized flow of breathing gas from gas flow generator 6, generally indicated by arrow D, is delivered via a delivery conduit 12 to a patient interface device 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 1 shown in FIG. 2 is what is known as a single-limb system, meaning that the patient circuit includes only delivery conduit 12 connecting patient 10 to pressure support system 1. As such, an exhaust vent is provided in patient interface device 14 for venting exhaled gases from the system. It should be noted that the exhaust vent can be provided at other locations in addition to or instead of in patient interface device 14, such as in delivery conduit 12. It should also be understood that the exhaust vent can have a wide variety of configurations depending on the desired manner in which gas is to be vented from pressure support system 1.

The present invention also contemplates that pressure support system 1 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

In the illustrated embodiment, pressure support system 1 includes a pressure controller in the form of a valve 16 provided in an internal delivery conduit 18 provided in pressure generating device base unit 4 of pressure support system 1. Valve 16 controls the pressure of the flow of breathing gas from gas flow generator 6 that is delivered to patient 10. For present purposes, gas flow generator 6 and valve 16 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 16 is optional depending on the technique used to control the pressure of the flow of breathing gas delivered to patient 10. If valve 16 is eliminated, the pressure generating system corresponds to gas flow generator 6 alone, and the pressure of gas in the patient circuit is controlled, for example, by controlling the motor speed of gas flow generator 6.

Pressure support system 1 further includes a flow sensor 20 that measures the flow of the breathing gas within delivery conduit 18 and delivery conduit 12. In the particular embodiment shown in FIG. 1, flow sensor 20 is interposed in line with delivery conduits 18 and 12, most preferably downstream of valve 16. Flow sensor 20 generates a flow signal, $Q_{MEASURED}$, that is provided to a controller 22 and is used by controller 22 to determine the flow of gas at patient 10 ($Q_{PATIENT}$).

Techniques for calculating $Q_{PATIENT}$ based on $Q_{MEASURED}$ are well known, and take into consideration the pressure drop of the patient circuit, known leaks from the system, i.e., the intentional exhausting of gas from the circuit as described herein, and unknown (unintentional) leaks from the system, such as leaks at the mask/patient interface. The present invention contemplates using any known or hereafter developed technique for calculating total leak flow $Q_{LEAK}$, and using this determination in calculating $Q_{PATIENT}$ based on $Q_{MEASURED}$ (and for other purposes as described elsewhere herein). Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 16.

Controller 22 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 1.

An input/output device 24 is provided for setting various parameters used by airway pressure support system 1, as well as for displaying and outputting information and data to a user, such as a clinician or caregiver.

Furthermore, in the illustrated embodiment, pressure support system 1 also includes a humidifier 17 provided in the main housing of pressure support system 1. Alternatively, humidifier 17 may be separate from and located external to the main housing. Humidifier 17 is controlled by controller 22. Humidifier 17 further improves comfort by providing moisture in the supplied gas. In the exemplary embodiment, humidifier 17 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

Continuing to refer to FIG. 2, pressure support system 1 includes a heating control unit 50 included in pressure support system base unit 4. Conduit 12 includes first and second resistive wires 61, 62 that extend along conduit 12. A thermistor 63 is also included in conduit 12. First and second resistive wires 61, 62 are electrically coupled between heating control unit 50 and thermistor 63. Heating control unit 50 is structured to operate in a first mode to use first and second resistive wires 61,62 to heat airflow in conduit 12 and a second mode to use first and second resistive wires 61,62 and thermistor 63 to sense temperature of airflow in conduit 12, as will be described in more detail herein.

In the exemplary embodiment, patient interface device 14 includes a patient sealing assembly 28, which in the illustrated embodiment is a nasal mask. However, other types of patient sealing assemblies, such as, without limitation, a nasal/oral mask, a nasal cushion, or a full face mask, which facilitate the delivery of the flow of breathing gas to the airway of a patient may be substituted for patient sealing assembly 28 while remaining within the scope of the present invention. Patient sealing assembly 28 includes a cushion 30 coupled to a frame member 32. In the illustrated embodiment, cushion 30 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, frame member 32 is made of a rigid or semi-rigid material, such as, without limitation, an injection molded thermoplastic or silicone, and includes a faceplate portion 34 to which cushion 30 is fluidly attached. A fluid coupling conduit 36 having an exhaust vent is coupled to an opening in faceplate portion 34 to allow the flow of breathing gas from pressure generating device base unit 4 to be communicated to an interior space defined by cushion 30, and then to the airway of a patient.

Frame member 32 also includes a forehead support member 38 that is coupled to the faceplate portion 34 by a connecting member 40. A forehead cushion 42 is coupled to the rear of forehead support 38. In the exemplary embodiment, forehead cushion 42 is made of a material that is similar to the material of cushion 30.

Patient interface device 14 also includes a headgear component 44 for securing patient interface device 14 to the head of patient 10. Headgear component 44 includes a back member 46, upper strap members 48 and lower strap members 49. In the exemplary embodiment, upper strap members 48 and lower strap members 49 each include a hook and loop fastening system, such as VELCRO®, provided on the end thereof to allow headgear component 44 to be secured in a known manner. It will be understood that the described hook and loop fastening arrangement is meant to be exemplary only, and that other selectively adjustable fastening arrangements are also possible within the scope of the present invention.

In the illustrated, non-limiting exemplary embodiment of the present invention, airway pressure support system 1 essentially functions as a CPAP pressure support system, and, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 3:
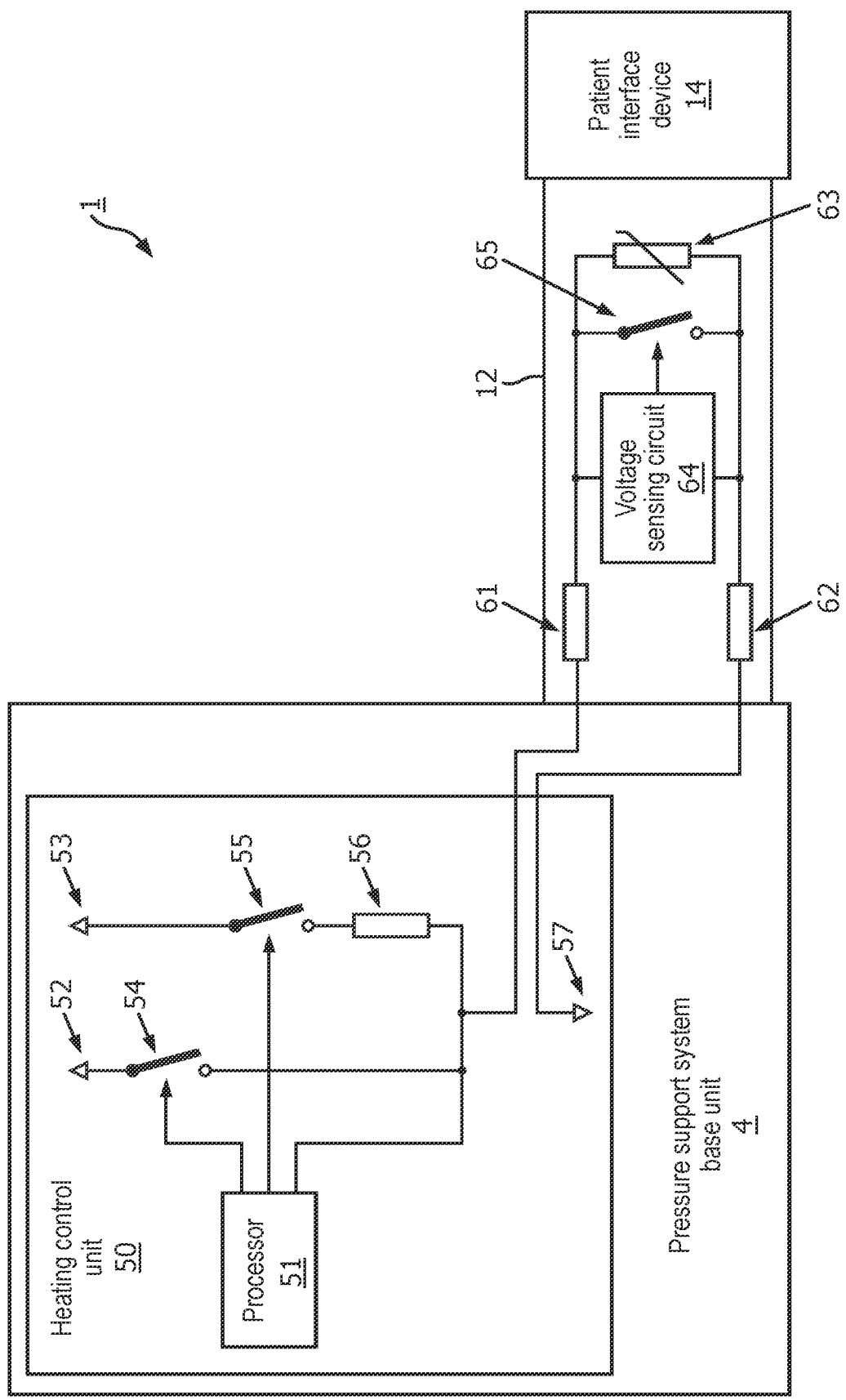
FIG. 3 is a schematic diagram of an airway pressure support system having a voltage sensing circuit in a conduit according to an exemplary embodiment.

FIG. 3 is a schematic diagram of pressure support system 1 in accordance with an exemplary embodiment. Pressure support system 1 in FIG. 3 is simplified to more clearly illustrate and explain the operation of heating control unit 50. For example, several features of pressure support system base unit 4 and patient interface device 14 that have been shown and described with respect to FIG. 2 are omitted from FIG. 3.

In the exemplary embodiment of FIG. 3, heating control unit 50 includes a processor 51. Heating control unit 50 also includes a first voltage source 52, a second voltage source 53, a first switch 54, a second switch 55, and neutral reference point 57 (e.g., without limitation, a ground). Heating control unit 50 may also include a pull-up resistor 56. First voltage source 52 has a higher voltage level than second voltage source 53. In some exemplary embodiments, first voltage source 52 has a voltage of about 12 or 24 VDC, or within a range of about 12-24 VDC, and second voltage source 53 has a voltage of about 3.3 or 5 VDC, or within a range of about 3.3-5 VDC. However, it will be appreciated by those having ordinary skill in the art that any suitable voltages may be selected for first and second voltage sources 52,53.

Conduit 12 includes first and second resistive wires 61,62 and thermistor 63. First and second resistive wires 61,62 extend along conduit 12 and are electrically connected between heating control unit 50 and thermistor 63. A voltage sensing circuit 64 and a third switch 65 are also included in conduit 12. Third switch 65 is electrically connected in parallel with thermistor 63. The state of third switch (i.e., open or closed) is controlled by voltage sensing circuit 64.

First switch 54 is electrically coupled between first voltage source 52 and first resistive wire 61. Second switch 55 is electrically coupled between second voltage source 53 and first resistive wire 61. Pull-up resistor 56 may be electrically connected between second switch 55 and first resistive wire 61. Processor 51 is structured to control states of first and second switches 54,55.

Heating control unit 50 is structured to operate in a first mode to use first and second resistive wires 61,62 to heat airflow in conduit 12 and a second mode to use first and second resistive wires 61,62 and thermistor 63 to sense temperature of airflow in conduit 12. In the first mode, processor 51 controls first switch 54 to close and second switch 55 to open. When first switch 54 is closed, voltage from first voltage source 52 is applied to first resistive wire 61. Voltage sensing circuit 64 is structured to sense voltage applied to first resistive wire 61 and, in response to sensing that the voltage of first voltage source 52 is applied to first resistive wire 61, voltage sensing circuit 64 is structured to close third switch 65. When third switch 65 is closed, current passes through third switch 65 from first resistive wire 61 to second resistive wire 62, bypassing thermistor 63. Current continues through second resistive wire 62 to neutral reference point 57, which is electrically connected to second resistive wire 62. When third switch 65 is closed and thermistor 63 is bypassed, the voltage from first voltage source 52 applied to first resistive wire 61 causes current to flow through first and second resistive wires 61,62 heating them and, thus, heating airflow in conduit.

In an exemplary embodiment, the voltage sensing circuit 64 may include a voltage divider and third switch 65 may be an electrically controlled switch such as a transistor. The voltage divider may be structured to output a voltage level sufficient to turn on third switch 65 when heating control unit 50 is operating in the first mode and insufficient to turn on third switch 65 when heating control unit 50 is operating in the second mode. It will be appreciated by those having ordinary skill in the art that the components and arrangement of components in voltage sensing circuit 61 may be any suitable components arranged in any suitable manner to implement the functionality of voltage sensing circuit 64.

In the second mode, processor 51 controls second switch 55 to close and first switch 54 to open. When second switch 55 is closed, voltage from second voltage source 53 causes current to flow through pull-up resistor 56 to first resistive wire 61. Voltage sensing circuit 64 is structured to open third switch 65 when it senses that a voltage less than first voltage source 52 is applied to first resistive wire 61. When third switch 65 is open, current flowing through first resistive wire 61 flows through thermistor 63 and second resistive wire 62 to neutral reference point 57. Processor 51 is electrically connected to first resistive wire 61 and is structured to sense a voltage between first resistive wire 61 and pull-up resistor 56. When third switch 65 is open and current flows through thermistor 63, the voltage sensed by processor 51 is indicative of the temperature of airflow in the conduit 12 sensed by thermistor 63. Thus, processor 51 is able to sense temperature of airflow in conduit 12 when heating control unit 50 is operating in the second mode.

The first and second resistive wires 61,62 are both used to heat airflow in conduit 12 and to sense temperature of airflow in conduit 12 via thermistor 63. A separate third resistive wire is not needed.

Figure 4:
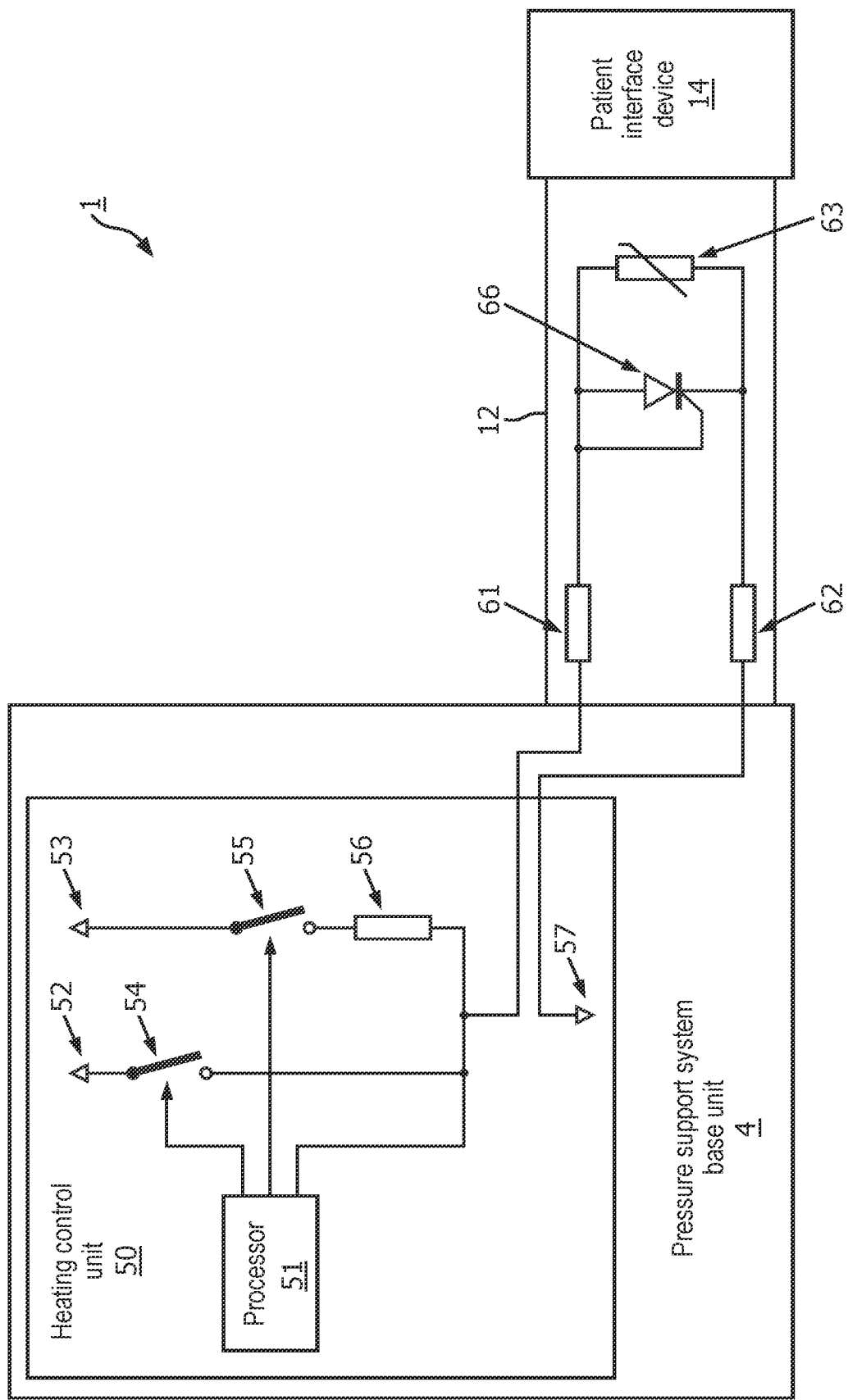
FIG. 4 is a schematic diagram of an airway pressure support system having a silicon controlled rectifier in a conduit according to an exemplary embodiment.

FIG. 4 is a schematic diagram of pressure support system 1 in accordance with an exemplary embodiment. Pressure support system 1 of FIG. 4 is similar to pressure support system 1 of FIG. 3. However, in pressure support system 1 of FIG. 4, voltage sensing circuit 64 and third switch 65 are omitted and instead a silicon controlled rectifier (SCR) 66 is electrically connected in parallel with thermistor 63.

SCR 66 includes an anode and gate electrically connected to first resistive wire 61 and a cathode electrically connected to second resistive wire 62. SCR 66 has a gate to cathode trigger voltage that is high enough so that SCR 66 does not trigger when heating control unit 50 is operating in the second mode (i.e., first switch 54 is open and second switch 55 is closed), but is low enough such that SCR 66 triggers when heating control unit 50 is operating in the first mode (i.e., first switch 54 is closed and second switch 55 is open). When heating control unit 50 is operating in the first mode, SCR 66 is triggered and turns on, thus allowing current to flow through SCR 66 from first resistive wire 61 to second resistive wire 62 bypassing thermistor 63 and heating first and second resistive wires 61,62 and airflow in conduit 12. When heating control unit 50 is operating in the second mode, SCR 66 is turned off and current flows from first resistive wire 61 to second resistive wire 62 via thermistor 63, thus allowing processor 51 to sense temperature of airflow in conduit 12 via thermistor 63.

Figure 5:
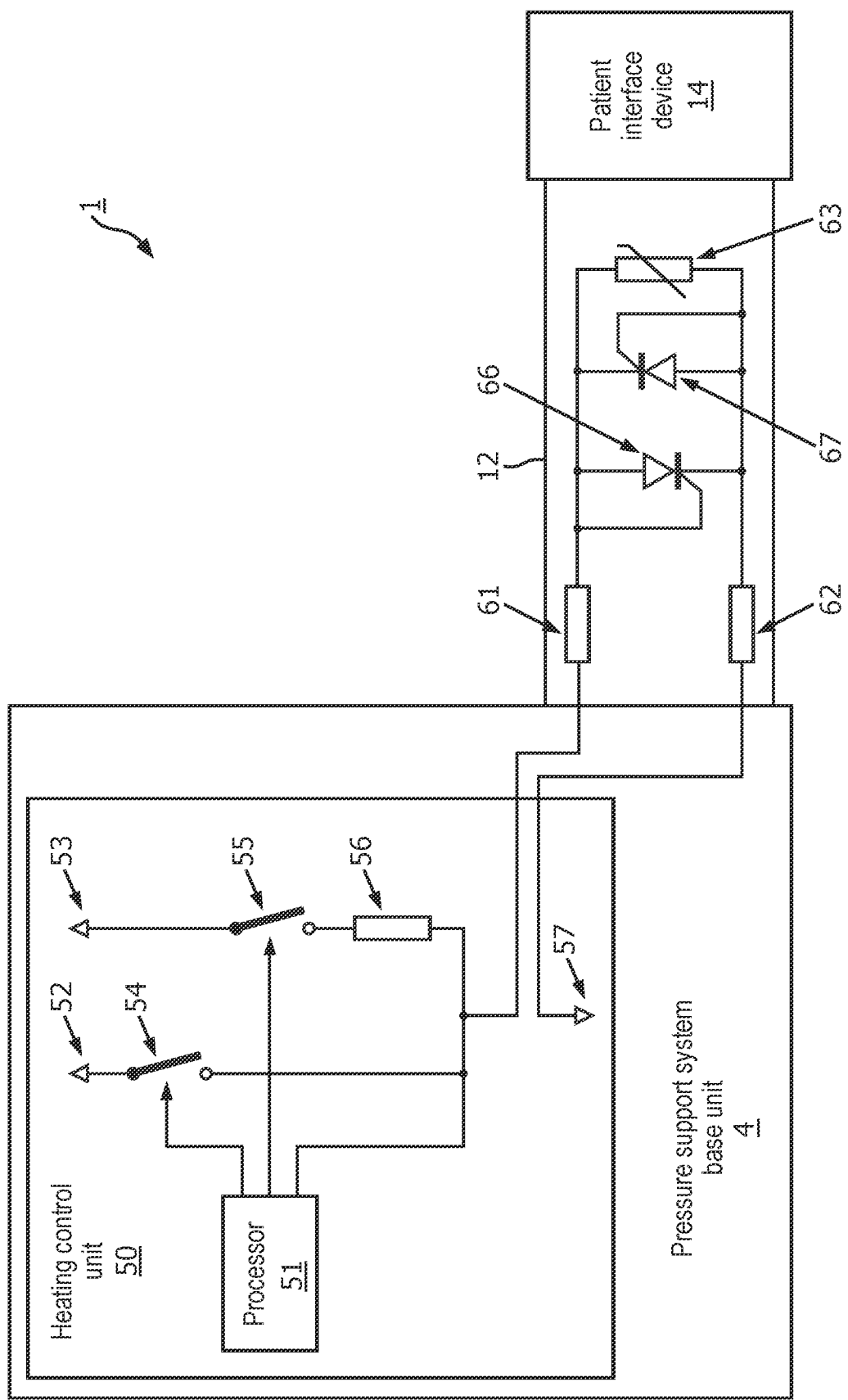
FIG. 5 is a schematic diagram of an airway pressure support system having two silicon controlled rectifiers in a conduit according to an exemplary embodiment.

FIG. 5 is a schematic diagram of pressure support system 1 in accordance with an exemplary embodiment. Pressure support system 1 of FIG. 5 is similar to pressure support system 1 of FIG. 4. However, in pressure support system 1 of FIG. 5, a second SCR 67 is electrically connected in parallel with thermistor 63 in addition to first SCR 66.

First SCR 66 includes an anode and gate electrically connected to first resistive wire 61 and a cathode electrically connected to second resistive wire 62. Second SCR 67 includes a cathode electrically connected to first resistive wire 61 and an anode and gate electrically connected to second resistive wire 62. First SCR 66 has a gate to cathode trigger voltage that is high enough so that first SCR 66 does not trigger when heating control unit 50 is operating in the second mode, but is low enough such that first SCR 66 triggers when heating control unit 50 is operating in the first mode. Second SCR 67 has a gate to cathode trigger voltage that is about the same as first SCR 66.

In the arrangement shown in FIG. 5, first SCR 66 will trigger and turn on when heating control unit 50 is operating in the first mode and will turn off when heating control unit 50 is operating in the second mode. The exemplary embodiment of FIG. 5 also allows bipolar operation. That is, the connections of first and second resistive wires 61,62 to heating control unit 50 can be switched. For example, first resistive wire 61 can be connected to neutral reference point 57 and second resistive wire 62 can be electrically coupled to first and second voltage sources 52,53 via first and second switches 54,55, thus reversing the polarity of first and second resistive wires 61,62. When the polarity is reversed, second SCR 67 will trigger and turn on when heating control unit 50 is operating in the first mode and will turn on when heating control unit 50 is operating in the second mode. Current flowing through first and second resistive wires 61,62 will heat first and second resistive wires 61,62 and airflow in conduit 12, and will bypass thermistor 63 by flowing through second SCR 67 when heating control unit 50 is operating in the first mode. Current flowing through first and second resistive wires 61,62 will flow through thermistor 63 allowing processor 51 to sense temperature of airflow in conduit 12 when heating control unit 50 operates in the second mode.

Bipolar operation allows heating control unit 50 to operate in the first and second modes regardless of whether its connections to first and second resistive wires 61,62 are switched. Thus, a connector between first and second resistive wires 61,62 and heating control unit 50 does not need to be oriented in a particular way to operate properly. The connector can be flipped and the system will continue to operate properly.

Figure 6:
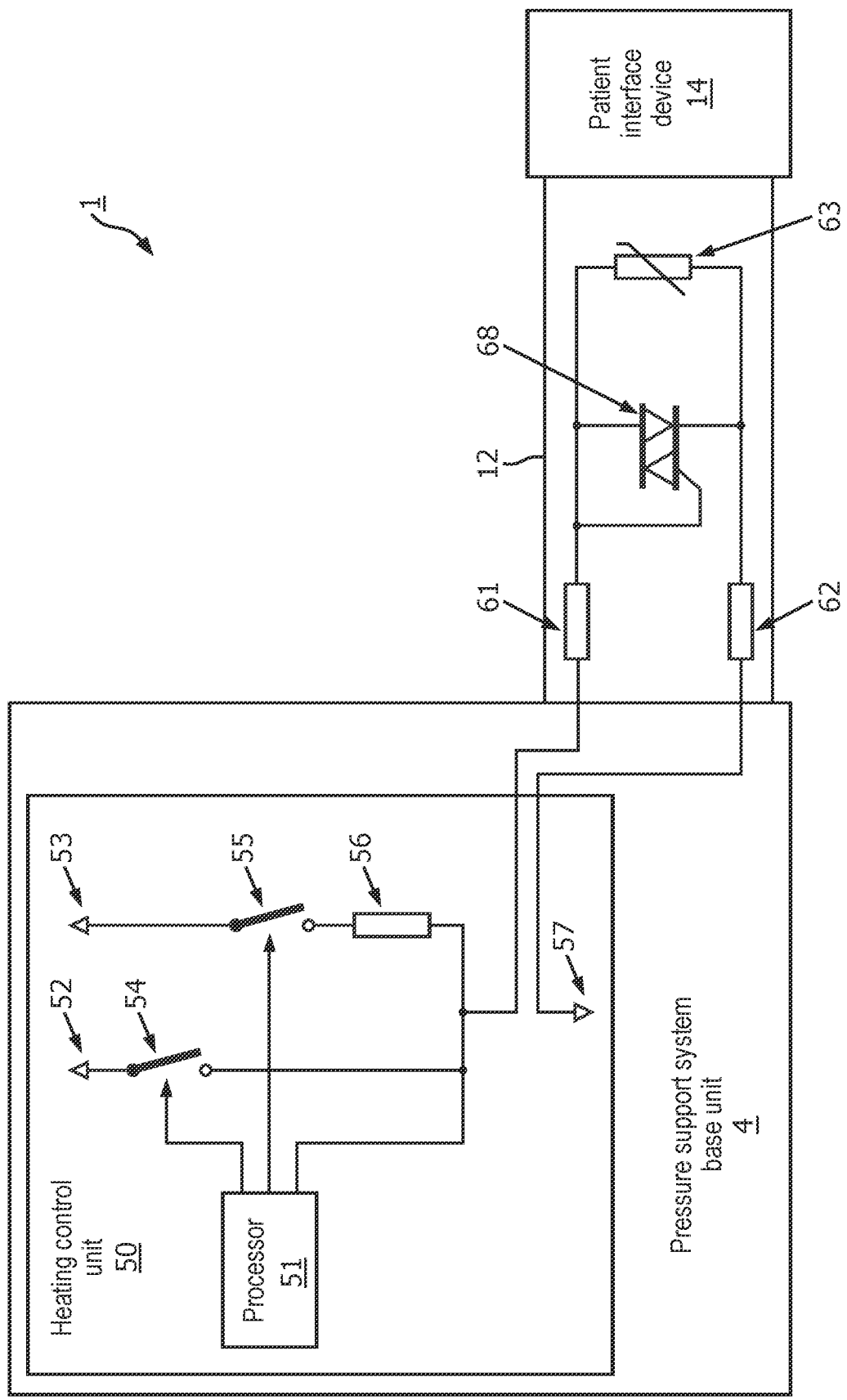
FIG. 6 is a schematic diagram of an airway pressure support system having a TRIAC in a conduit according to an exemplary embodiment.

FIG. 6 is a schematic diagram of pressure support system 1 in accordance with an exemplary embodiment. Pressure support system 1 of FIG. 6 is similar to pressure support system 1 of FIG. 5. However, in pressure support system 1 of FIG. 6, a TRIAC 68 is electrically connected in parallel with thermistor 63 instead of first and second SCRs 66,67.

TRIAC 68 has a first anode electrically connected to first resistive wire 61 and a second anode electrically connected to second resistive wire 62. TRIAC 68 also has a gate electrically connected to first resistive wire 61. TRIAC 68 has a gate to anode trigger voltage that is high enough so that TRIAC 68 does not trigger when heating control unit 50 is operating in the second mode, but is low enough such that TRIAC 68 triggers and turns on when heating control unit 50 is operating in the first mode. In the arrangement shown in FIG. 6, TRIAC 68 will trigger and turn on when heating control unit 50 is operating in the first mode and will turn off when heating control unit 50 is operating in the second mode.

The exemplary embodiment of FIG. 6, similar to the exemplary embodiment of FIG. 5, allows bipolar operation. For example, when TRIAC 68 turns on, current may flow in a direction from first resistive wire 61 to second resistive wire 62 or from second resistive wire 62 to first resistive wire 61 through TRIAC 68 and bypass thermistor 63. Heating control unit 50 may operate in the first and second modes regardless of whether its connections to first and second resistive wires 61,62 are switched. Thus, a connector between first and second resistive wires 61,62 and heating control unit 50 does not need to be oriented in a particular way to operate properly. The connector can be flipped and the system will continue to operate properly.

Figure 7:
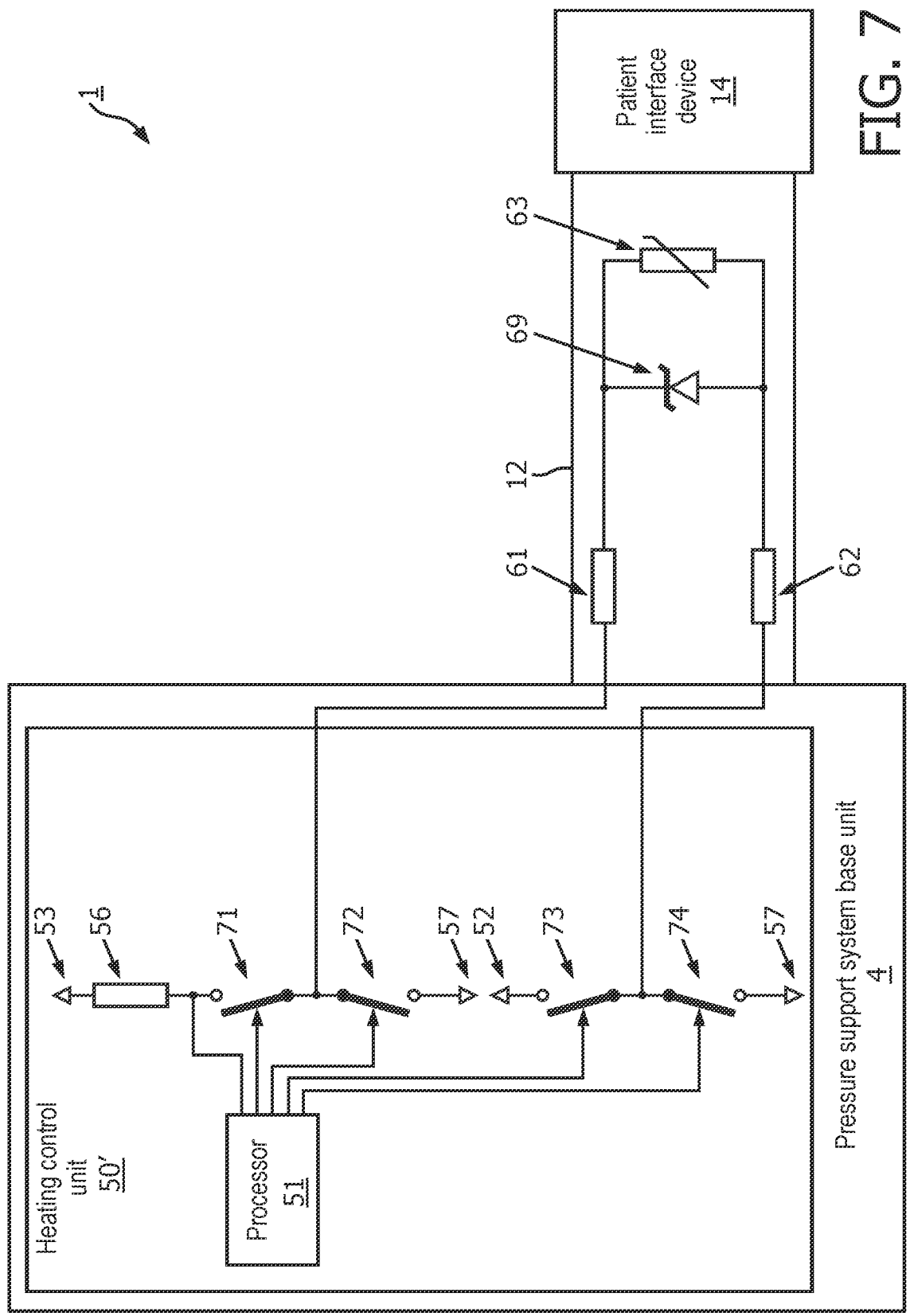
FIG. 7 is a schematic diagram of an airway pressure support system with an alternative heating control unit according to an exemplary embodiment.

FIG. 7 is a schematic diagram of pressure support system 1 in accordance with an exemplary embodiment. Pressure support system 1 of FIG. 7 is similar to pressure support system 1 of FIG. 3. However, pressure support system 1 of FIG. 7 includes a heating control unit 50' having an alternative design. Pressure support system 1 of FIG. 7 also includes a diode 69 electrically connected in parallel with thermistor 63 rather than voltage sensing unit 64 and third switch 65. Diode 69 includes an anode electrically connected to second resistive wire 62 and a cathode electrically connected to first resistive wire 61.

Heating control unit 50' includes processor 51, first voltage source 52, second voltage source 53, pull-up resistor 56, and neutral reference point 57. Heating control unit 50' also includes a first switch 71, a second switch 72, a third switch 73, and a fourth switch 74. First switch 71 is electrically coupled between second voltage source 53 and first resistive wire 61. Second switch 72 is electrically coupled between neutral reference point 57 and first resistive wire 61. Third switch 73 is electrically coupled between first voltage source 52 and second resistive wire 62. Fourth switch 74 is electrically coupled between neutral reference point 57 and second resistive wire 62.

Processor 51 is structured to control states of first through fourth switches 71,72,73,74. Heating control unit 50' is structured to operate in a first mode to use first and second resistive wires 61,62 to heat airflow in conduit 12 and a second mode to use first and second resistive wires 61,62 and thermistor 63 to sense temperature of airflow in conduit 12. In the first mode, processor 51 controls first and fourth switches 71,74 to open and second and third switches 72,73 to close. In this mode, voltage from first voltage source 52 is applied to second resistive wire 62 causing current to flow from second resistive wire 62 through diode 69 to first resistive wire 61, bypassing thermistor 63, and on to neutral reference point 57. In the second mode, processor 51 controls first and fourth switches 71,74 to close and second and third switches 72,73 to open. In this mode, voltage from second voltage source 53 is applied to first resistive wire 61 causing current to flow from first resistive wire 61 through thermistor 63 to second resistive wire 62 and on to neutral reference point 57. Processor 51 is electrically connected at a point between pull-up resistor 56 and first resistive wire 61 and is structured to sense a voltage at this point that is indicative of the temperature of airflow in conduit 12 sensed by thermistor 63.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system for delivering a flow of breathing gas to an airway of a patient, comprising:
    a base unit structured to generate the flow of breathing gas and including a heating control unit;
    a conduit coupled to the base unit and structured to carry the flow of breathing gas;
    a thermistor disposed in the conduit; and
    first and second resistive wires extending along the conduit from the base unit to the thermistor,
    wherein the heating control unit is structured to selectively operate in a first mode to heat the conduit using the first and second resistive wires and a second mode to sense a temperature of airflow in the conduit with the thermistor via the first and second resistive wires; and
    wherein the heating control unit includes:
        a first voltage source having a first voltage level;
        a first switch electrically coupled between the first voltage source and a first end of the first resistive wire;
        a second voltage source having a second voltage level that is less than the first voltage level;
        a second switch electrically coupled between the second voltage source and the first end of the first resistive wire;
        a neutral reference point electrically connected to the second resistive wire; and
        a processor structured to control the first and second switches to selectively open and close such that the first and second voltage sources are selectively connected to the neutral reference point.

2. The pressure support system of claim 1, wherein the processor is structured to control the first switch to close and the second switch to open when the heating control unit is operating in the first mode and to control the first switch to open and the second switch to close when the heating control unit is operating in the second mode.

3. The pressure support system of claim 1, further comprising:
    a voltage sensing circuit disposed in the conduit and electrically connected to the first and second resistive wires; and
    a third switch disposed in the conduit and electrically connected in parallel with the thermistor,
    wherein the voltage sensing circuit is structured to sense a voltage level of the first resistive wire and to control the third switch based on the sensed voltage level, wherein the voltage sensing circuit is structured to control the third switch to open in response to sensing that the voltage level of the first resistive wire is less than the first voltage level of the first voltage source and to otherwise control the third switch to close.

4. The pressure support system of claim 1, further comprising: a silicon controlled rectifier electrically connected in parallel with the thermistor, wherein the silicon controlled rectifier includes a gate electrically connected to one of the first and second resistive wires.

5. The pressure support system of claim 1, further comprising:
    a first silicon controlled rectifier electrically connected in parallel with the thermistor; and
    a second silicon controlled rectifier electrically connected in parallel with the thermistor, wherein the first silicon controlled rectifier includes a gate electrically connected to the first resistive wire and the second silicon controlled rectifier includes a gate electrically connected to the second resistive wire.

6. The pressure support system of claim 5, wherein the first silicon controlled rectifier includes an anode electrically connected to the first resistive wire and a cathode electrically connected to the second resistive wire, and wherein the second silicon controlled rectifier includes an anode electrically connected to the second resistive wire and a cathode electrically connected to the first resistive wire.

7. The pressure support system of claim 1, further comprising: a TRIAC electrically connected in parallel with the thermistor, wherein the TRIAC includes a gate electrically connected to one of the first and second resistive wires.

8. The pressure support system of claim 1, wherein the processor is electrically connected to the first resistive wire and is structured to sense the temperature from the thermistor.

9. The pressure support system of claim 1, wherein the first voltage level is in a range of about 12-24 VDC, and wherein the second voltage level is in a range of about 3.3-5 VDC.

10. A method of heating airflow in a conduit of a pressure support system, the method comprising:
    providing a base unit structured to generate a flow of breathing gas and including a heating control unit, the conduit coupled to the base unit and structured to carry the flow of breathing gas, a thermistor disposed in the conduit, and first and second resistive wires extending along the conduit from the base unit to the thermistor;
    operating the heating control unit in a first mode to heat the conduit using the first and second resistive wires;
    operating the heating control unit in a second mode to sense a temperature of airflow in the conduit with the thermistor via the first and second resistive wires; and
    providing, in the heating control unit, a first voltage source having a first voltage level, a first switch electrically coupled between the first voltage source and a first end of the first resistive wire, a second voltage source having a second voltage level that is less than the first voltage level, a second switch electrically coupled between the second voltage source and the first end of the first resistive wire, a neutral reference point electrically connected to the second resistive wire, and a processor structured to control the first and second switches to selectively open and close such that the first and second voltage sources are selectively connected to the neutral reference point.

11. The method of claim 10, wherein operating the heating control unit in a first mode to heat the conduit using the first and second resistive wires includes controlling the first switch to close and the second switch to open, and wherein operating the heating control unit in a second mode to sense a temperature of airflow in the conduit with the thermistor via the first and second resistive wires includes controlling the first switch to open and the second switch to close.

12. The method of claim 10, further comprising:
    providing a voltage sensing circuit disposed in the conduit and electrically connected to the first and second resistive wires, and a third switch disposed in the conduit and electrically connected in parallel with the thermistor;
    sensing a voltage level of the first resistive wire with the voltage sensing circuit;
    controlling the third switch to open when the sensed voltage level of the first resistive wire is less than the first voltage level of the first voltage source; and
    controlling the third switch to close when the sensed voltage level of the first resistive wire is not less than the first voltage level of the first voltage source.

13. The method of claim 10, further comprising:
    providing a silicon controlled rectifier electrically connected in parallel with the thermistor and having a gate electrically connected to one of the first and second resistive wires.

14. The method of claim 10, further comprising:
    providing a TRIAC electrically connected in parallel with the thermistor and having a gate electrically connected to one of the first and second resistive wires.

* * * * *